(12) United States Patent
Lynn

(10) Patent No.: US 10,426,855 B2
(45) Date of Patent: Oct. 1, 2019

(54) SYSTEM AND METHOD FOR THE DECONTAMINATION OF INDOOR AIR AND SURFACES HAVING BIOLOGICAL, CHEMICAL OR PHYSICAL CONTAMINATION

(71) Applicant: Daniel W. Lynn, Omaha, NE (US)

(72) Inventor: Daniel W. Lynn, Omaha, NE (US)

( * ) Notice: Subject to any disclaimer, the term of this patent is extended or adjusted under 35 U.S.C. 154(b) by 289 days.

(21) Appl. No.: 15/583,164

(22) Filed: May 1, 2017

(65) Prior Publication Data

US 2018/0311396 A1    Nov. 1, 2018

(51) Int. Cl.
| | | |
|---|---|---|
| *A61L 9/00* | (2006.01) | |
| *B01D 9/00* | (2006.01) | |
| *B01D 47/02* | (2006.01) | |
| *A61L 2/20* | (2006.01) | |
| *A61L 9/015* | (2006.01) | |

(52) U.S. Cl.
CPC ............... *A61L 2/202* (2013.01); *A61L 9/015* (2013.01); *A61L 2202/11* (2013.01); *A61L 2202/14* (2013.01); *A61L 2202/25* (2013.01); *A61L 2209/11* (2013.01); *A61L 2209/212* (2013.01)

(58) Field of Classification Search
CPC ........ A61L 2/0017; A61L 2/183; A61L 2/202; A61L 9/20; A61K 8/22
USPC ................. 422/5, 28, 120, 186.07, 305–306; 239/34, 690; 261/76, 78.1
See application file for complete search history.

(56) References Cited

U.S. PATENT DOCUMENTS

| | | | |
|---|---|---|---|
| 4,857,240 A * | 8/1989 | Kearnes ................. | A61L 9/122 261/26 |
| 6,153,105 A | 11/2000 | Tadlock et al. | |
| 6,334,328 B1 | 1/2002 | Brill | |
| 6,685,825 B1 | 2/2004 | Chang | |
| 8,071,526 B2 | 12/2011 | Lynn | |
| 8,075,705 B2 | 12/2011 | Lynn | |
| 9,068,149 B2 | 6/2015 | Lynn | |
| 9,151,528 B2 | 10/2015 | Erbs et al. | |
| 9,174,845 B2 | 11/2015 | Lynn | |
| 9,522,348 B2 | 12/2016 | Lynn | |
| 2004/0004042 A1 | 1/2004 | Hadley et al. | |
| 2004/0168989 A1 | 9/2004 | Tempest, Jr. | |
| 2009/0142225 A1 | 6/2009 | Tornqvist | |
| 2010/0219137 A1 | 9/2010 | Lacasse | |
| 2011/0085934 A1 * | 4/2011 | Joshi ...................... | A23L 3/3409 422/5 |
| 2013/0193081 A1 | 8/2013 | Vasiliu et al. | |
| 2014/0263097 A1 | 9/2014 | Lynn | |
| 2016/0251243 A1 | 9/2016 | Lynn | |

\* cited by examiner

*Primary Examiner* — Monzer R Chorbaji
(74) *Attorney, Agent, or Firm* — Dennis L. Thomte; Thomte Patent Law Office LLC

(57) ABSTRACT

A system and method for the decontamination of indoor air and surfaces having biological, chemical or physical contamination wherein the system is mounted on a wall or the like in the area to be treated. An ozone gas generator is positioned within the housing of the system for generating ozone gas in the housing. The housing also includes an exhaust fan assembly which exhausts the ozone gas and air mixture from the housing into the area to be treated. The system may be operated continuously or at predetermined times and for predetermined lengths of time.

9 Claims, 5 Drawing Sheets

SYSTEM AND METHOD FOR THE DECONTAMINATION OF INDOOR AIR AND SURFACES HAVING BIOLOGICAL, CHEMICAL OR PHYSICAL CONTAMINATION

BACKGROUND OF THE INVENTION

Field of the Invention

This invention relates to a system for the decontamination of indoor air and surfaces having biological, chemical or physical contaminants. More particularly, the system of this invention attacks odor causing substances and their source to remove odors in treatment areas without the use of chemicals or masking deodorizers.

Description of the Related Art

Odors arise from the decomposition products of meat or fish protein, containing sulfur, nitrogen and oxygen, as well as spoilage microorganisms that belong to four major groups: bacteria, viruses, protozoa or fungi. Infectious diseases caused by disease-causing microbes are responsible for more deaths worldwide than any other single cause. Scientists are working hard to find ways that will control these germs but trying to defeat them is not an easy task. Disease-causing microbes are very good at adjusting to new environments making it hard to find a way to get rid of them. Microbes can quickly develop new features that make them resistant to the drugs that were once able to kill them. This means scientists must try and stay one-step ahead, even though it is hard to do. New diseases caused by recently discovered pathogens are also being identified at an increasing rate. In the past 30 years, about 30 new pathogens have been identified. Disease-causing microbes can also be called pathogens, germs or bugs and are responsible for causing infectious diseases.

Odors can also arise from fires, (incomplete combustion), fats, chemicals, etc. The smells that humans react to most strongly are associated with food odor sensations which are often the result of a complex interaction of many, sometimes hundreds, of chemical compounds on the sensory organs of the nose. The smell in a modern office building is a "cocktail" made up of the smells of more than a thousand substances (sweat, tobacco, carpeting, cleansers, plants, ink, etc.).

The total smell perceived is often different from, and sometimes stronger than, the sum of its parts. Bad smells can cause health effects, such as headache, nausea and sleeplessness. Bad odor compounds are generally not poisonous, at least not in the concentrations at which they begin to cause an odor nuisance.

Common inorganic agents, such as sodium hypochlorite, hydrogen peroxide, potassium permanganate and ozone can readily oxidize most of the usual odor compounds.

In general, the cheapest of these is sodium hypochlorite (chlorine bleach). The extent of poisoning caused by chlorine depends on the amount of chlorine a person is exposed to, how the person was exposed, and the length of time of the exposure. When chlorine gas comes into contact with moist tissues, such as the eyes, throat, and lungs, an acid is produced that can damage these tissues. Industrially, hydrogen peroxide has been used for years to deodorize, disinfect and neutralize hazardous pollutants.

Ozone is a very powerful oxidizing agent. Ozone in water decomposes to oxygen and hydroxyl radicals, each of which has a higher oxidation potential than either ozone or chlorine. The activity of hydroxyl radical is enhanced by a higher pH. Ozone can oxidize odorous organic and inorganic compounds in the presence of water. Also, in the presence of moisture, it is a power germicide. It can also directly oxidize odorous compounds by attacking double bonds or a reactive site.

In a hotel situation, with so many people frequenting one place with no closing hours, or reprieve for it to be fully cleaned out and ventilated, hotels are bound to be riddled with a whole selection of different substances and situations which will cause some very unpleasant and problematic hotel odors. These hotel odors need to be dealt with rapidly and efficiently, as new guests are arriving constantly and a good first impression and the comfort of the guests is of paramount importance in such a situation. With so many areas where hotel odors can occur, it is vital that the system of odor control is able to maintain the required standards while at the same time is affordable and requires little time and energy to be inputted into the system.

In the walk-in cooler situation, chemical reactions that cause offensive sensory changes in foods are mediated by a variety of microbes that use food as a carbon and energy source. These organisms include prokaryotes (bacteria), single-celled organisms lacking defined nuclei and other organelles, and eukaryotes, single-celled (yeasts) and multicellular (molds) organisms with nuclei and other organelles. Some microbes are commonly found in many types of spoiled foods white others are more selective in the foods they consume; multiple species are often identified in a single spoiled food item but there may be one species (a specific spoilage organism, SSO) primarily responsible for production of the compounds causing off odors and flavors. Within a spoiling food, there is often a succession of different populations that rise and fall as different nutrients become available or are exhausted. Some microbes, such as lactic acid bacteria and molds, secrete compounds that inhibit competitors. Spoilage microbes are often common inhabitants of soil, water, or the intestinal tracts of animals and may be dispersed through the air and water and by the activities of small animals, particularly insects. It should be noted that with the development of new molecular typing methods, the scientific names of some spoilage organisms, particularly the bacteria, have changed in recent years and some older names are no longer in use. Many insects and small mammals also cause deterioration of food but these will not be considered here.

If the concentration of an odor in air is below levels of irritation (levels known to cause eye, nose, or throat irritation in people), the symptoms will pass when you move out of the exposure area.

Many types of devices have been previously provided to reduce odors in indoor areas such as restaurant kitchens, bathrooms, grocery stores, classrooms, school locker rooms, office buildings, homes, veterinary clinics, hospitals, hotels, etc. However, those prior art devices utilize chemicals or masking deodorizers. Further, the prior art deodorizing devices are not believed to be able to disinfect air and contact surfaces while deodorizing the area in which the prior art deodorizing devices are placed. Further, it is believed that the prior art deodorizing devices will not effectively treat bacteria, viruses, mildew, molds, allergens, smoke odors, or food preparation odors.

If the concentration of an odor in air is at or above levels of irritation and the exposure duration is longer, the symptoms may last after moving out of the exposure area.

It is a principal object of this invention to provide a powerful indoor odor control system which is designed to disinfect air and contact surfaces while eliminating odors.

A further object of the invention is to provide an indoor odor control system which is safe to use.

Yet another object of the invention is to provide an indoor odor control system which is quiet in operation.

Yet another object of the invention is to provide an indoor odor control system which is easy to maintain.

Yet another object of the invention is to provide an indoor odor control system which sanitizes air.

Yet another object of the invention is to provide an indoor odor control system which is an odor oxidizer.

Yet another object of the invention is to provide an indoor odor control system which has the germicidal power of triatomic oxygen.

Yet another object of the invention is to provide an indoor odor control system which is wall mountable.

Yet another object of the invention is to provide an indoor odor control system which includes an adjustable timer.

Yet another object of the invention is to provide an indoor odor control system which energy efficient.

Yet another object of the invention is to provide an indoor odor control system which may be used in restaurant kitchens, bathrooms, grocery stores, classrooms, school locker rooms, commercial office buildings, homes, veterinary clinics, hospitals, hotels, water damaged areas, and vehicles.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

A system and method is described for the decontamination of indoor air and surfaces having biological, chemical or physical contamination. The system of this invention includes a housing having a base unit and a cover hingedly secured thereto. The base unit includes a back wall, a top wall, a bottom wall, a first side wall, and a second side wall. The cover includes an upper end, a lower end, a first side and a second side. The cover is hingedly secured to one side of the base unit so as to be able to be moved between open and closed positions.

An ozone gas generator is positioned in the base unit and has an air inlet opening formed therein which is in communication with an air inlet opening formed in the base unit. The ozone gas generator includes an ozone gas discharge tube extending therefrom which has a discharge end. An electrical power cord extends from a source of electrical power into the base unit and is electrically connected to the ozone power generator to power the same. An electrical timer is positioned in an opening in the cover and electrical switch is positioned another opening in the cover. An electrical operated exhaust fan assembly is positioned in a third opening of the cover with the exhaust fan assembly having a discharge side which is in communication with the area around the housing. The exhaust fan assembly also has an air intake side which is in communication with the interior of the base unit when the cover is in its closed position whereby the ozone gas generated by the ozone gas generator will be exhausted from the housing through the discharge side of the exhaust fan assembly.

The switch is electrically connected to the power cord, the ozone gas generator, the timer and the exhaust fan assembly so as to be able to control the operation of the ozone gas generator, the timer and the exhaust fan assembly.

In the preferred embodiment, the switch is manually movable between Off, Timer, and On positions. The operation of the ozone gas generator and the exhaust fan assembly is controlled by the timer when the switch is in its Timer position. The timer is deactivated when the switch is in its On position so that the ozone generator and the exhaust fan assembly are continuously operated.

The ozone gas and air mixture discharged from the housing by the exhaust fan assembly decontaminates the indoor area and surfaces in the surrounding area which have biological, chemical or physical contaminants.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 1 is a perspective view illustrating the odor abatement and sanitizing system of this invention mounted on the wall of a room or the like;

DESCRIPTION OF THE PREFERRED EMBODIMENT

Figure 1:
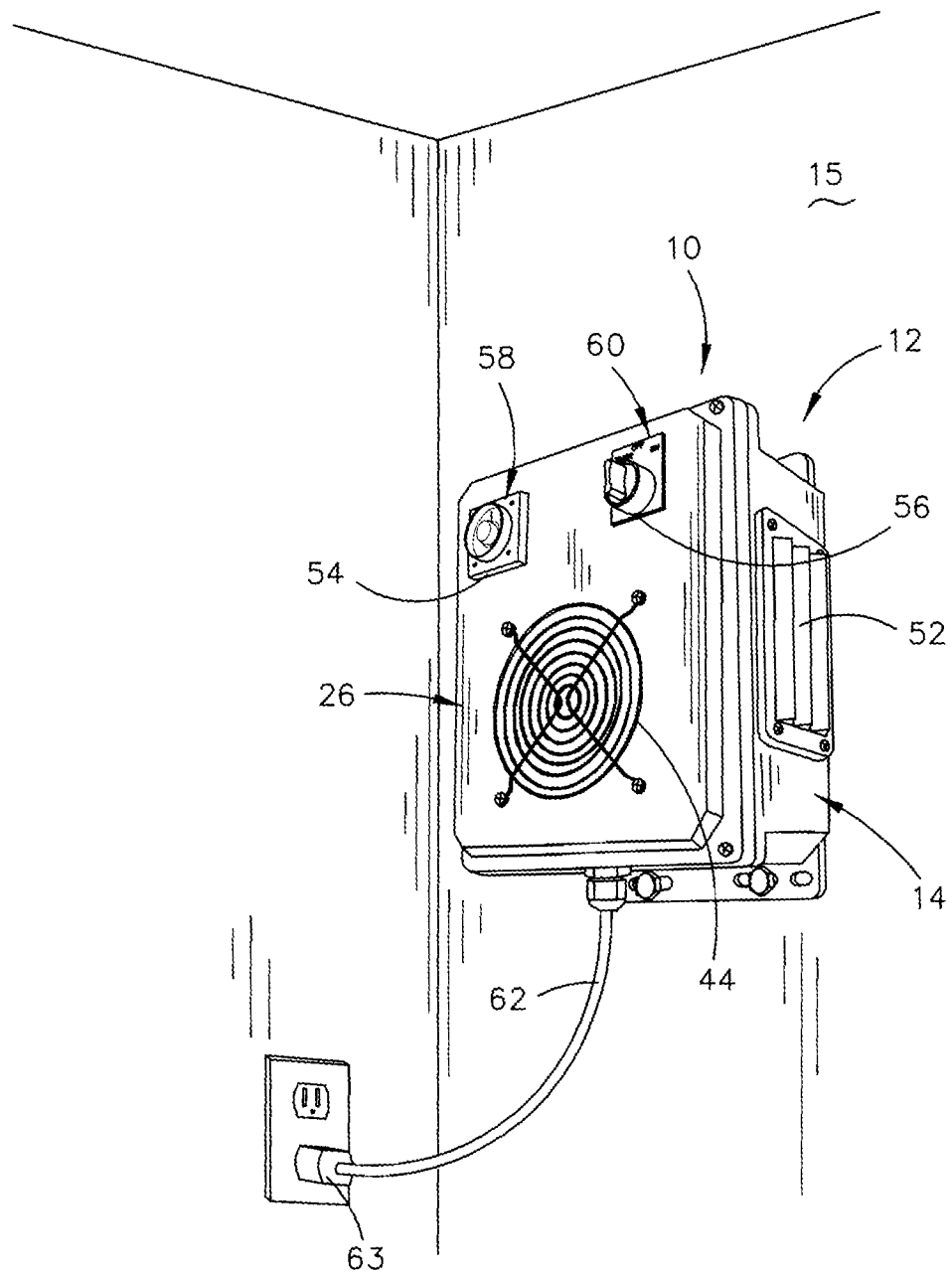
Figure 2:
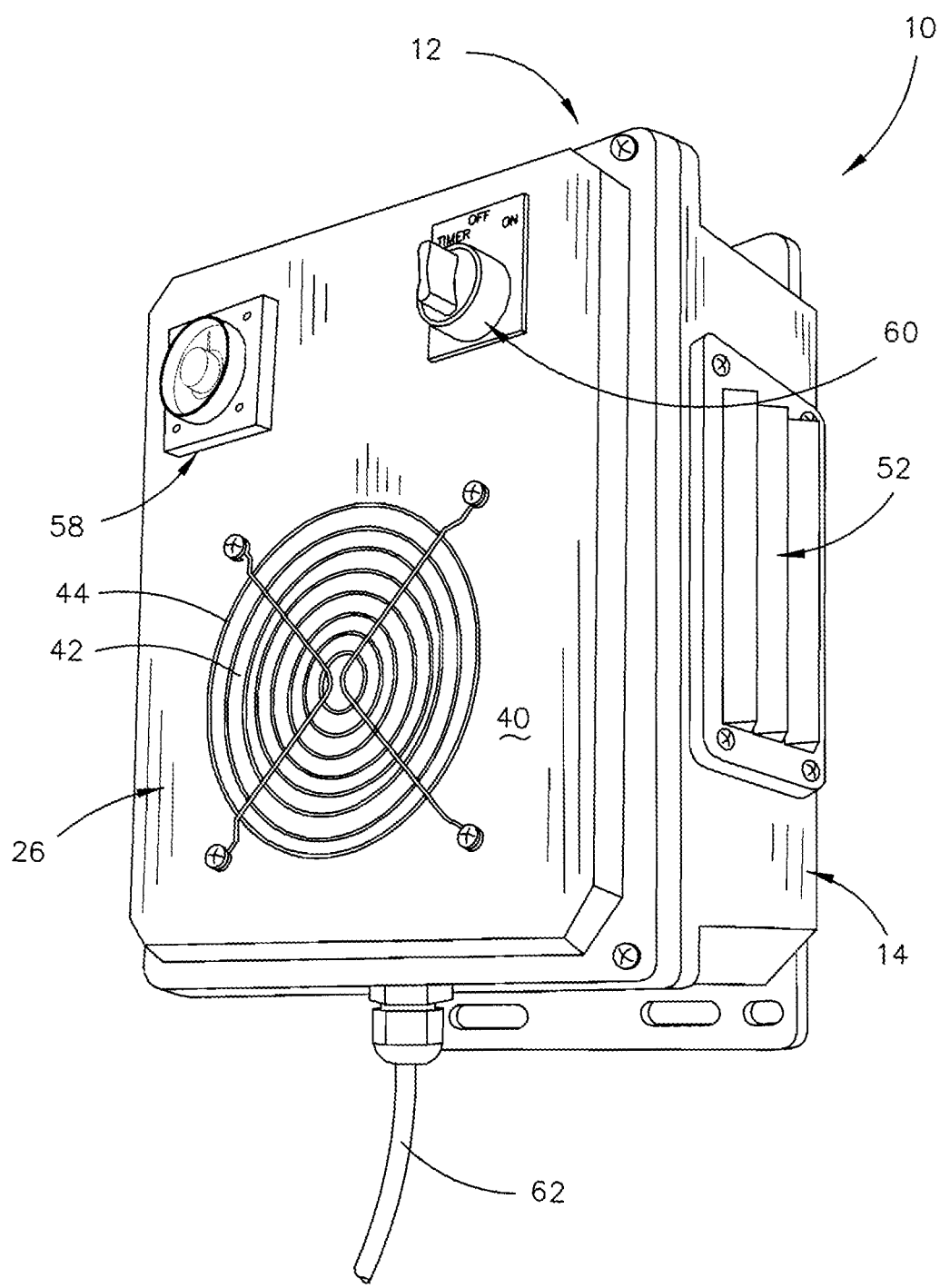
FIG. 2 is a front perspective view of the odor abatement and sanitizing system of this invention.
Figure 3:
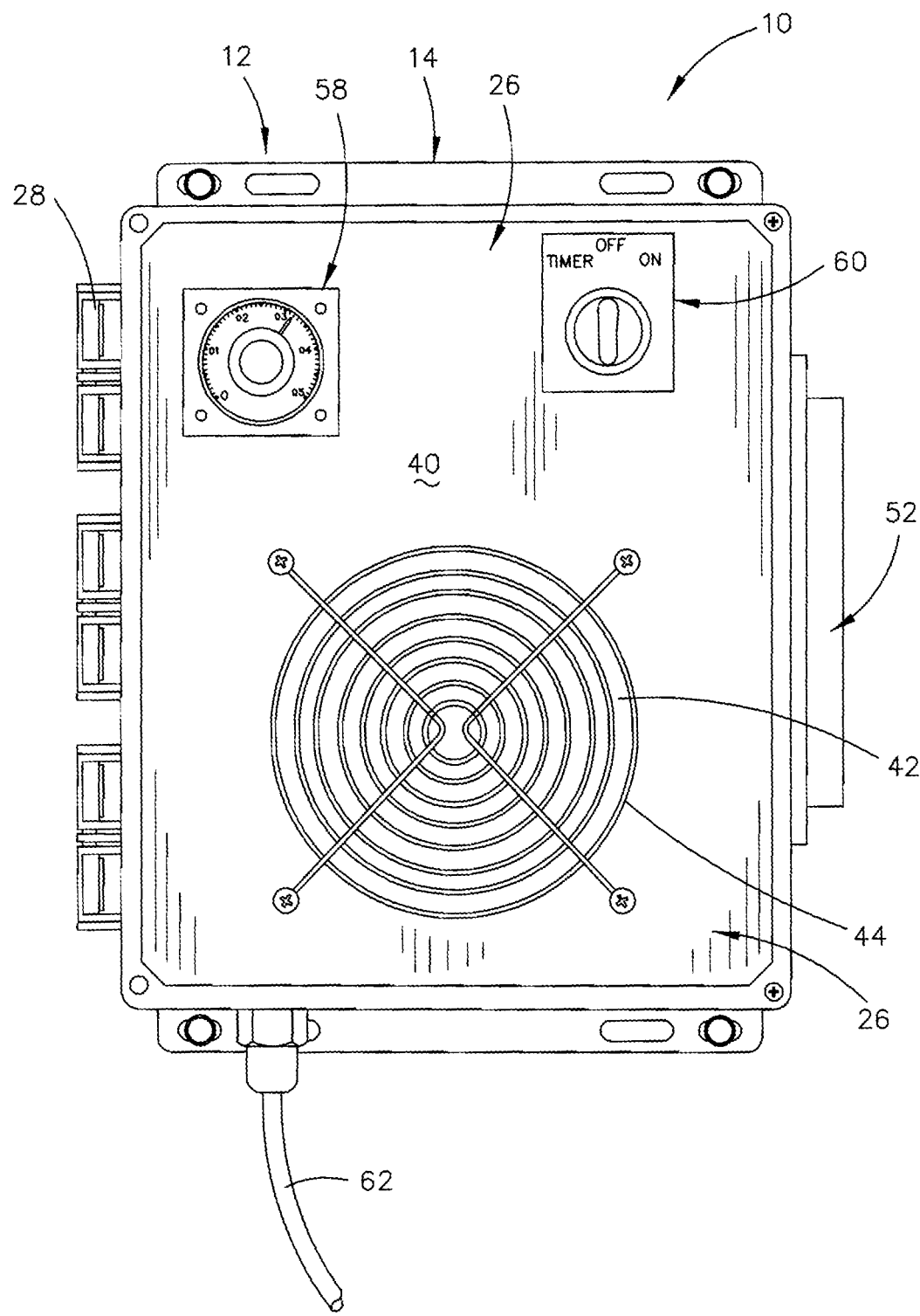
FIG. 3 is a front view of the odor abatement and sanitizing system of this invention.
Figure 4:
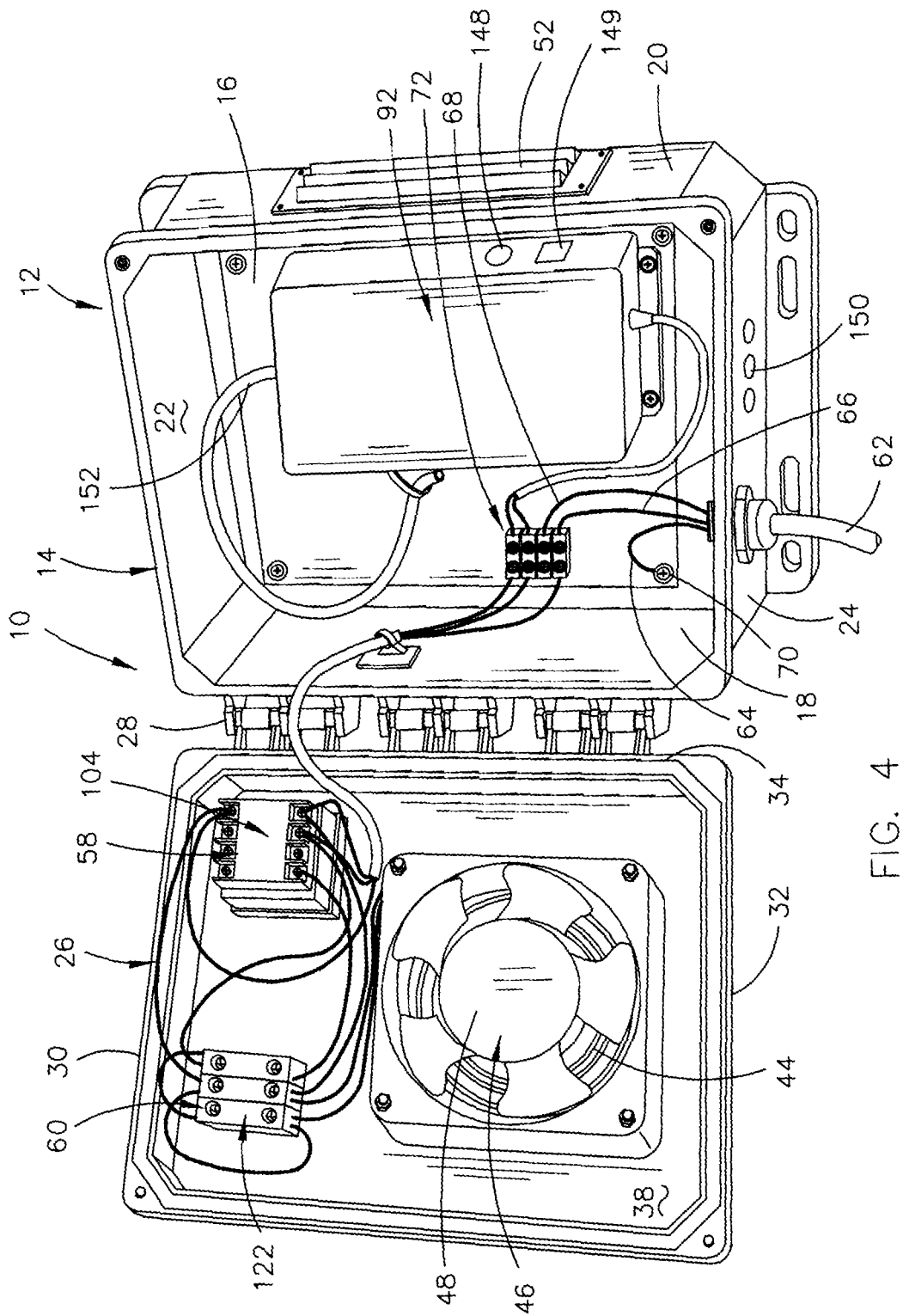
FIG. 4 is a perspective view of the odor abatement and sanitizing system of this invention with the cover thereof being in an open position.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The system of this invention is referred to generally by the reference numeral 10. System 10 includes a housing, an enclosure or cabinet 12. Housing 12 includes a base unit 14 which may be secured to or mounted on a vertically disposed supporting surface such as a wall 15 or the like. Base unit 14 includes a back wall 16, a first side wall 18, a second side wall 20, a top wall 22 and a bottom wall 24. A cover 26 is hingedly secured to the outer end of side wall 18 by a hinge assembly 28 to enable the cover 26 to be able to selectively close the outer open end of base unit 14. Cover 26 will be described as having an upper end 30, a lower end 32, a first side 34, a second side 36, an inner side 38 and an outer side 40.

Cover 26 has an exhaust opening 42 formed therein at its lower end with the cover 26 having a grill 44 secured thereto which extends over the opening 42. A conventional exhaust fan assembly 46 is secured to cover 26 at the inner side 38 thereof inwardly of opening 42. Fan assembly 46 has its air intake side 48 in communication with the interior of base unit 14 and has its air discharge side in communication with the opening 42 so that air within the housing 12 may be exhausted therefrom by way of the exhaust fan assembly 46.

Side wall 20 of base unit 14 has an air intake opening formed therein which is covered by a grill 52 extending thereover. Cover 26 has an opening 54 formed therein and an opening 56 formed therein. A timer 58 is mounted in opening 54. The preferred timer 58 is Model AT8N manufactured by Autonics of Busan, Korea and is generally referred to as a time delay relay. The time delay relay may be set for any desired time delays. A switch 60 is mounted in opening 56 in cover 26. Switch 60 is preferably manufactured by Weg Electric Corp. of Duluth, Ga. and is a Model Weg BC10. The switch 60 may be manually moved between Timer, Off and On positions. The timer 58, switch 60 and fan assembly 46 are wired as will be described in more detail hereinafter.

Power cord 62 is connected to a source of 110 volts power and includes three leads 64, 66 and 68. Lead 64 is grounded to the back wall 16 of base unit 14 at 70. The numeral 72 refers to a connector block which is preferably attached to the back wall 16 of base unit 14 by any convenient means. Connector block 72 includes connector terminals 74, 76, 78, 80, 82, 84, 86 and 88. Lead 66 of power cord 62 is connected to connector terminal 76 in conventional fashion. Lead 68 of power cord 62 is connected to connector terminal 80 in conventional fashion. One end of lead 90 is attached to connector terminal 84 and extends therefrom to an ozone gas generator 92. One end of lead 94 is attached to connector terminal 88 and extends therefrom to generator 92. The details of generator 92 will be described in more detail hereinafter.

One end of lead 96 is attached to connector terminal 86 and extends therefrom. One end of lead 98 is attached to connector terminal 82 and extends therefrom. Connector terminals 78 and 82 are electrically connected together by a jumper 100. One end of lead 102 is attached to connector terminal 74 and extends therefrom. Connector terminals 74 and 76 are configured to electrically and mechanically connect leads 102 and 66 together respectively. Connector terminals 78 and 80 are configured to electrically and mechanically connect lead 68 to one end of the jumper lead 100 which is connected to connector terminal 78. Connector terminals 82 and 84 are configured to electrically and mechanically connect lead 90 to the other end of jumper lead 100 which is connected to connector terminal 82. Connector terminals 86 and 88 are configured to electrically and mechanically connect leads 96 and 94 together.

The numeral 104 refers to the terminal block of timer 58. Terminal block 104 includes terminals 106, 108, 110, 112, 114, 116, 118 and 120. Lead 102 has one end connected to connector terminal 74 of connector block 72 and has its other end connected to terminal 110 of terminal block 104. Lead 98, which has one end connected to connector terminal 82 of block 72, has its other end secured to terminal 112 of terminal block 104.

The numeral 122 refers to the terminal block of switch 60. Terminal block 122 includes terminals 124, 126, 138, 130, 132 and 134. A lead 136 has one end connected to terminal 120 and has its other end connected to terminal 130. A jumper lead 138 has its ends secured to terminals 126 and 134 and extends therebetween. A lead 140 has one end secured to terminal 130 and has its other end secured to terminal 132. A lead 142 has one end secured to terminal 124 and has its other end secured to terminal 106. One end of lead 144 is secured to terminal 128 and has its other end secured to terminal 112. One end of lead 146 is secured to terminal 126 and has its other end secured to terminal 110. One end of lead 148 is secured to terminal 132 and has its other end secured to exhaust fan assembly 46. One end of lead 150 is secured to terminal 128 and has its other end secured to exhaust fan assembly 46.

Ozone gas generator 92 has an air inlet 148 formed in one side thereof inwardly of grill 52. A power switch 49 is also provided in the same side as the opening 148. The bottom wall 24 of base unit 14 preferably has a plurality of air inlet openings 150 formed therein. Generator 92 has a gas discharge tube 152 extending therefrom. The ozone gas generator 92 is preferably a Model ZO-30N gas ozone generator of Enaly which includes an integrated air pump, an air dryer and diffuser.

Figure 5:
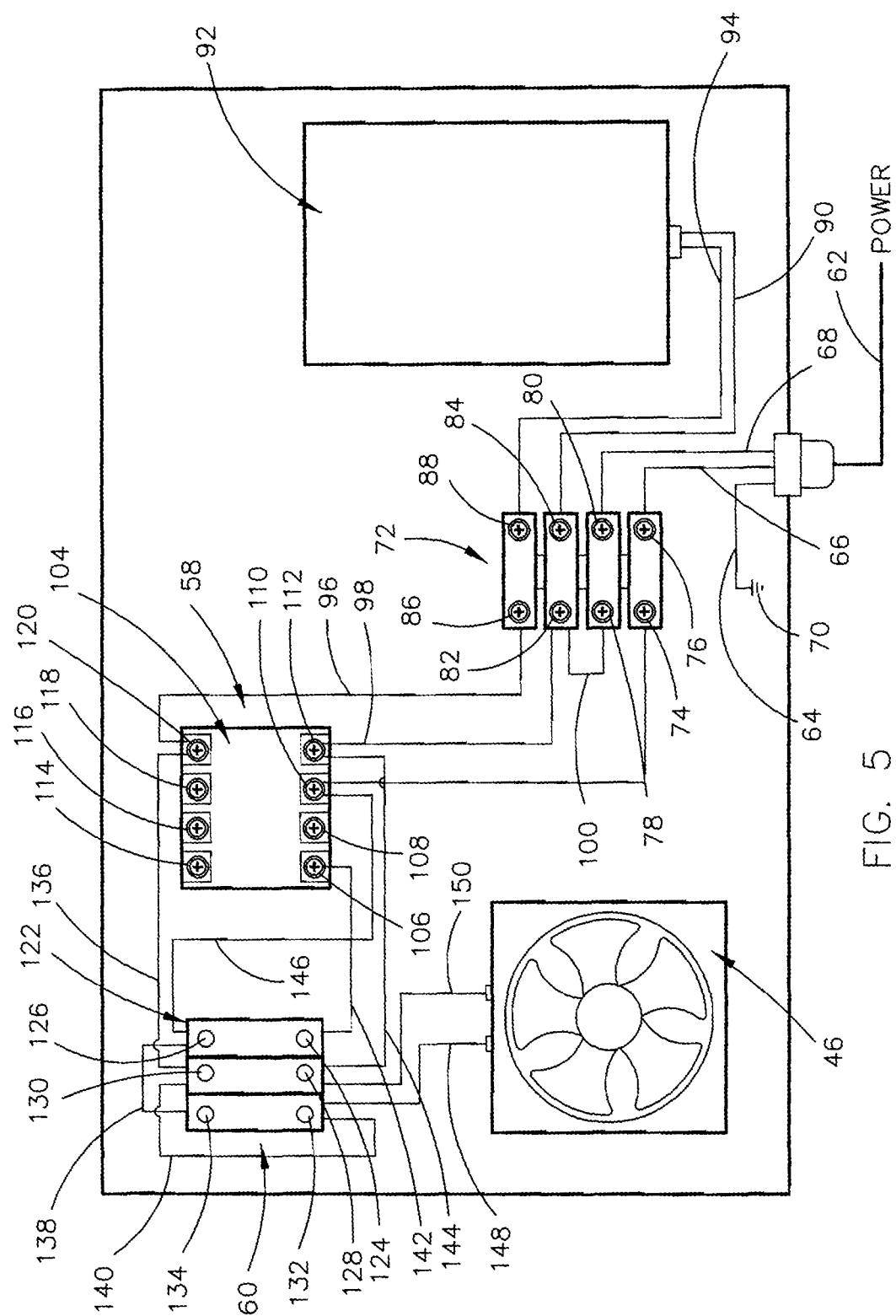
FIG. 5 is a schematic of the electrical circuitry of the odor abatement and sanitizing system of this invention.

In operation, the system 10 will be secured to a wall 15 in the area to be treated. The power cord 62 will then be connected to a source of power. The power cord is electrically connected to the various components of the system as disclosed herein above and as illustrated in FIG. 5. The switch 60 will initially be in the "OFF" position. When it is desired to decontaminate or disinfect the air within the area to be treated and/or to decontaminate the surfaces within the area to be treated, the switch 60 will be manually moved to either the "TIMER" position or the "ON" position. If the switch 60 is moved to its "ON" position, the ozone gas generator 92 and the exhaust fan assembly 46 will run continuously. When running, the exhaust fan assembly 46 will discharge air outwardly through the exhaust opening 42 in cover 26 and will draw air into the housing 12 through the grill 52 and through the openings 150. When the ozone gas generator 92 and the exhaust fan assembly 46 are running, the ozone gas generator 92 will discharge ozone gas from the discharge end of tube 152. When running, air will be drawn into the ozone gas generator 92 by way of opening 148. Tube 152 will discharge the ozone gas towards the intake side of the exhaust fan assembly 46 with the ozone gas and air mixture in housing 52 being discharged from the exhaust fan assembly 46 into the area to be treated. The ozone gas and air mixture will decontaminate or disinfect the air and surfaces within the area to be treated.

If the switch 60 is moved to its "TIMER" position, the ozone gas generator 92 and the exhaust fan assembly 46 will be operated at predetermined times for predetermined lengths of time.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. A system for the decontamination of indoor air and surfaces having biological, chemical or physical contamination;
   a housing including a base unit and a cover hingedly secured thereto;

said base unit including:
   (a) a back wall having an upper end, a lower end, a first side, a second side, a front side and a rear side;
   (b) a first side wall extending forwardly from said first side of said back wall and having an upper end, a lower end, a front end, a rear end, an inner surface and an outer surface;
   (c) a second side wall extending forwardly from said second side of said back wall and having an upper end, a lower end, a first end, a rear end, an inner surface and an outer surface;
   (d) a top wall extending forwardly from said upper end of said back wall and having a back end, a front end, a first end, a second end, an inner surface and an outer surface;
   (e) a bottom wall extending forwardly from said lower end of said back wall and having a back end, a front end, a first end, a second end, an inner surface and an outer surface;
   (f) said first side wall of said base unit having an air inlet opening formed therein;
said cover including:
   (a) a front wall having an upper end, a lower end, a first side, a second side, a front side and a rear side;
   (b) said first side of said cover being hingedly secured to said second side wall of said base unit whereby said cover may be selectively hingedly moved with respect to said base unit between a closed position and an open position;
   (c) said cover having first, second and third openings formed therein;
an ozone gas generator positioned in said base unit;
said ozone gas generator having an air inlet opening formed therein which is in communication with said air inlet opening of said base unit;
said ozone gas generator having an ozone gas discharge tube extending therefrom;
an electrical power cord extending from a source of electrical power into said base unit;
said power cord being electrically connected to said ozone gas generator to power the same;
an electrical timer positioned in said first opening of said cover;
an electrical switch positioned in said second opening of said cover;
an electrical operated exhaust fan assembly positioned in said third opening of said cover;
said exhaust fan assembly having a discharge side which is in communication with the area around said housing;
said exhaust fan assembly having an air intake side which is in communication with said base unit when said cover is in its said closed position whereby the ozone gas generated by said ozone gas generator will be exhausted from said housing through said discharge side of said exhaust fan assembly; and
said switch being electrically connected to said power cord, said ozone gas generator, said timer and said exhaust fan assembly so as to be able to control the operation of said ozone gas generator, said timer and said exhaust fan assembly.

2. The system of claim 1 wherein said switch is manually movable between Off, Timer and On positions.

3. The system of claim 2 wherein the operation of said ozone gas generator and said air exhaust fan assembly is controlled by said timer when said switch is in said Timer position.

4. The system of claim 2 wherein said timer is deactivated when said switch is in its said On position so that said ozone generator and said exhaust fan assembly are continuously operated.

5. The system of claim 1 wherein the discharge end of said ozone gas discharge tube is positioned closely adjacent said air intake side of said exhaust fan assembly when said cover is in its said closed position.

6. The system of claim 1 wherein a grill is positioned over said air intake opening in said cover.

7. The system of claim 1 wherein a grill is positioned over said third opening in said cover.

8. The system of claim 1 wherein said bottom wall of said base unit has one or more air intake openings formed therein.

9. The system of claim 1 wherein said housing is mounted on a wall.

* * * * *